United States Patent [19]
Gundersen

[11] Patent Number: 5,868,899
[45] Date of Patent: Feb. 9, 1999

[54] PROCESS LINE FOR THE PRODUCTION OF ABSORBENT DISPOSABLE ARTICLES

[75] Inventor: Dag H. Gundersen, Tolvsrød, Norway

[73] Assignee: SCA Hygiene Products AB, Gothenburg, Sweden

[21] Appl. No.: 750,039

[22] PCT Filed: May 23, 1995

[86] PCT No.: PCT/SE95/00582

§ 371 Date: Nov. 29, 1996

§ 102(e) Date: Nov. 29, 1996

[87] PCT Pub. No.: WO95/32694

PCT Pub. Date: Dec. 7, 1995

[30]   Foreign Application Priority Data

May 31, 1994 [SE]  Sweden ................................ 9401867

[51] Int. Cl.⁶ ...................................................... B32B 35/00
[52] U.S. Cl. .......................... 156/538; 156/349; 156/539; 156/543; 156/552; 156/598; 604/358
[58] Field of Search ..................... 156/349, 538, 156/539, 543, 552, 598; 604/358

[56]              References Cited

U.S. PATENT DOCUMENTS 5,383,988  1/1995  Hermann et al. .......................... 156/64
5,492,591  2/1996  Hermann et al. ........................ 156/538

FOREIGN PATENT DOCUMENTS 0 589 859  3/1994  European Pat. Off. .

OTHER PUBLICATIONS

"More than 60 Years of Teamwork Sets The Trend for Curt G. Joa, Inc." *Nonwovens Industry*, May 1994, p.42.

Nonwovens Mark., (1994) vo. 9, No. 21, 21 Oct. 1995, abstract only.

"W&D Offering New Sanitary Napkin Machinery," *Nonwovens Industry*, May 1994, pp. 72–73.

*Nonwovens Industry*, ad from diatec, Oct. 1995, p. 81.

*Primary Examiner*—Jeff H. Aftergut
*Attorney, Agent, or Firm*—Young & Thompson

[57]              ABSTRACT

A production line for manufacturing absorbent disposable articles, such as diapers, sanitary napkins and incontinence guards includes a conveyor path (3, 14, 15) which functions to move a web of material through the production line, and a row of devices (1, 4, 5, 6, 7, 8, 9, 11, 12, 13) which are arranged sequentially in the direction of movement of the conveyor path and which function to perform different working operations in the manufacture of the absorbent articles. The working devices are carried by rectangular carrier plates (29, 34, 35, 39) which are fastened to vertical posts (17) which, in a framework (16), are placed on the same side of the conveyor path and sequentially in a direction parallel with the direction of conveyor path movement. The production line includes carrier plates (29, 34, 35, 39) of mutually different sizes, wherein the length of each side of a carrier plate is essentially a multiple of the length of the smallest side of the smallest carrier plate (34, 35).

11 Claims, 2 Drawing Sheets

PROCESS LINE FOR THE PRODUCTION OF ABSORBENT DISPOSABLE ARTICLES

FIELD OF THE INVENTION

The present invention relates to a production line for the manufacture of absorbent disposable articles, such as diapers, sanitary napkins and incontinence guards, wherein the production line includes a conveyor path on which a web of material is moved through the production line, and a row of mutually sequential devices are arranged in the direction of web movement for carrying out different operations included in the manufacture of the absorbent article, these devices being carried on rectangular support plates which are attached to vertical posts which are placed in a framework on mutually the same side of the conveyor path and sequentially in a direction which extends parallel with the direction of path movement.

BACKGROUND OF THE INVENTION

Absorbent disposable articles are typically produced by taking a web of material from a storage reel and moving the web past a number of devices which perform different operations in sequence, such as placing absorbent bodies on the web, laying-out elastic, applying glue, applying further webs of material, compressing absorbent bodies, and heat-welding or ultrasonic-welding devices, and so on. In production of this nature, the production line has been traditionally constructed as one single unit. In recent times, production development has accelerated within this particular technical field, necessitating comprehensive reconstruction of the production lines. However, production lines of unit construction are less suitable for reconstruction and as a result, it has taken much too long to introduce new or modified products onto the market, and it has often been necessary to refrain from making small improvements to existing products, because of the radical changes in the production lines that such an improvement would occur, while, at the same time, the long nonproductive times caused by such reconstruction would prevent the demand of such products on the market being met, resulting in loss in profits and, in the longer term, perhaps also a loss in the share of the market.

The European Patent Application No. 93850174.9 teaches a production line for the manufacture of absorbent disposable articles which overcomes these drawbacks to a great extent. The various working devices of the production line are carried by mutually identical module plates which can be mounted in any desired position in a framework which extends along the production line. This design greatly facilitates reconstruction of the production line, while enabling the production line to be radically increased by adding further working devices thereto, without needing to make large modifications.

SUMMARY OF THE INVENTION

The primary object of the present invention is to facilitate still further reconstruction of a production line and the addition of further working devices, in comparison with the aforesaid known production line. A secondary object of the invention is to enable the carrier plates to be mounted in the production line more easily and enable the work to be carried out by unskilled workmen.

In accordance with the present invention, these objects are achieved with a production line of the kind defined in the introduction which is characterized in that the production line includes carrier plates of mutually different sizes; in that the length of each side of a carrier plate is essentially a multiple of the length of the smallest side of the smallest carrier plate; in that the distance between the vertical posts is essentially a multiple of the length of the smallest side of the smallest carrier plate; and in that each carrier plate includes a pair of opposing sides whose lengths are essentially equal to or essentially form a multiple of the smallest distance between the posts. This construction enables the carrier plates to be given to a very large extent a size which corresponds to the size of the working device carried thereby, therewith reducing the space required on the framework for the carrier plate carrying the working device as compared with a carrier plate which is dimensioned to support the largest working device in the production line, this carrier plate being the plate which determines the size of all other plates when only plates of one size are used. A production line constructed in accordance with the invention therewith provides a high degree of flexibility with regard to restructuring of the production line and the addition of further working devices, and also enables the available space on the framework to be used very effectively.

In a preferred embodiment of the invention, the smallest distance between the framework posts is essentially equal to twice the length of the smallest side of the smallest carrier plate, and the smallest side of the smallest carrier plate has a length of at least 400 mm. Furthermore, the mutually adjacent sides of mutually adjacent carrier plates are positioned on the framework with a gap of at least 2 mm therebetween. Each working-device drive means or operating means is carried by the same carrier plate as the working device concerned, and the framework includes at least one row of sets of connectors for delivering flowing media, such as electric current, air, etc., these connector sets being disposed sequentially in the movement direction of the conveyor path, wherein the connector sets are separated by a distance which is equal to a multiple of the distance between the vertical posts, and wherein a working device mounted on a carrier plate is provided with one or more connector elements for connection to one or more of the connectors included in said connector sets. Each set of connectors on the framework includes a databus connection and each working device includes a control means which can be connected to the databus connection. Furthermore, each carrier plate that carries a working device also includes a connector-element holder, this holder being placed in an identical position on each carrier plate. In one variant, at least one of the carrier plates that carries a working device includes more than one holder, these holders being placed sequentially along one side-edge part of the carrier plate. In this embodiment of the production line, each working device is mounted in the line by fastening an associated carrier plate to the framework and connecting the connector-element carried by the holder to the nearest of the fixed connector sets arranged on the framework. Working devices included in the product line can thus be mounted very easily and by technically unqualified personnel.

In one advantageous variant of the invention, the outer sides of the framework are clad with wall elements, of which carrier plates fastened to the vertical posts form a wall such as to enclose the interior of the framework, and the production line includes means for cooling the thus defined interior space.

BRIEF DESCRIPTION OF THE DRAWINGS

The invention will now be described with reference to the accompanying drawings, in which.

DETAILED DESCRIPTION OF THE INVENTION

Figure 1:
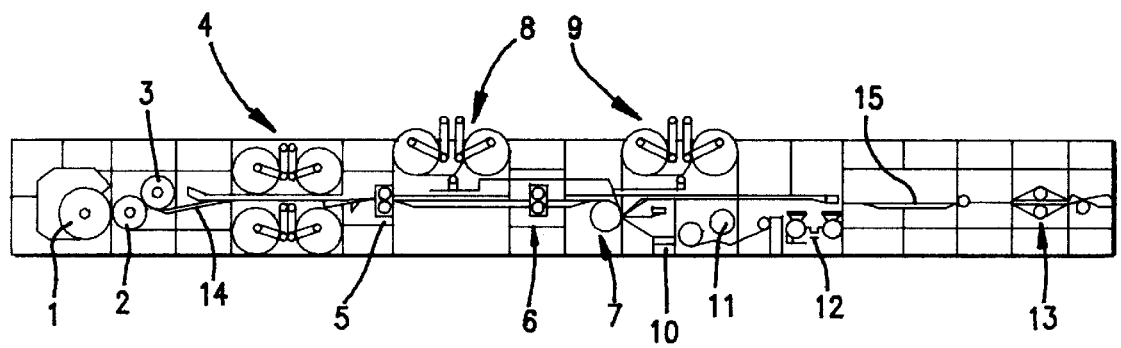
FIG. 1 is a schematic front view of one embodiment of an inventive production line.

FIG. 1 illustrates very schematically a diaper production line which, as seen in the production direction, i.e. from left to right in the Figure, includes a mat-laying wheel 1, a compression wheel 2, a transfer wheel 3, a device 4 for advancing layers from a top and a bottom reel-stand, a pair of compression rolls 5, a transverse cutter 6, a transfer device 7, advancing devices 8, 9, a thread applicator 10, an adhesive tape applicator 11, advancing means 12, and a cutter 13. The production line also includes means for conveying the diaper blank through the line, for instance the conveyors 14, 15 illustrated schematically in the Figure.

When manufacturing a diaper in the aforedescribed production line, the mat-laying wheel 1 produces a layer of cellulose fluff which is transferred to the conveyor 14 with the aid of the compression wheel 2 and the transfer wheel 3. The fibre mat then passes through the device 4, in which a top and a bottom layer of tissue taken from storage reels are delivered to the top and the bottom of the cellulose fluff mat or layer respectively. These layers then pass together through the roll pair 5 and are compressed therebetween. This results in a coherent, continuous three-layer body which passes through the transverse cutter 6, which produces individual absorbent bodies from the continuous, coherent three-layer body. A transfer wheel 7, also called an accelerator wheel, places the absorbent body on a web of plastic film, for instance polyethylene film, which is taken from a storage reel in the forward feed device or advancing device 12 and advanced to the wheel 7 from right to left in the Figure, and thereafter from left to right in said Figure with the individual absorbent bodies positioned a given distance apart. Prior to reaching the wheel 7, the plastic film passes the adhesive tape applicator 11, which provides the plastic film with a pair of fastener tapes, and will also have passed the thread applicator 10 which provides the plastic film with appropriate elastic. The forward feed devices 8, 9 function to lay two layers of nonwoven fabric, taken from reel stands included in said devices, on top of the plastic film web and the absorbent bodies, and the top and bottom layers are fastened together in some suitable way, for instance by gluing or ultrasonic welding. Finally, the web of absorbent bodies enclosed between top layers, i.e. the two nonwoven layers, and bottom sheet, i.e. the plastic film, pass through a cutter 13 with which finished diapers are cut from the web.

Appropriate working devices of a known kind can be chosen for performing the aforesaid functions by one of normal competence in this field, and the design of the working devices 1–13 and the conveyors 14, 15 included in the production line will naturally depend on the type of diaper to be manufactured. The design, or construction, of the individual working devices forms no part of the present invention and the application will not therefore be laden with a more detailed description of the components included in the production line.

In accordance with the present invention, the aforesaid working devices in the production line are mounted on carrier plates which, in turn, are mounted on a framework 16.

Figure 2:
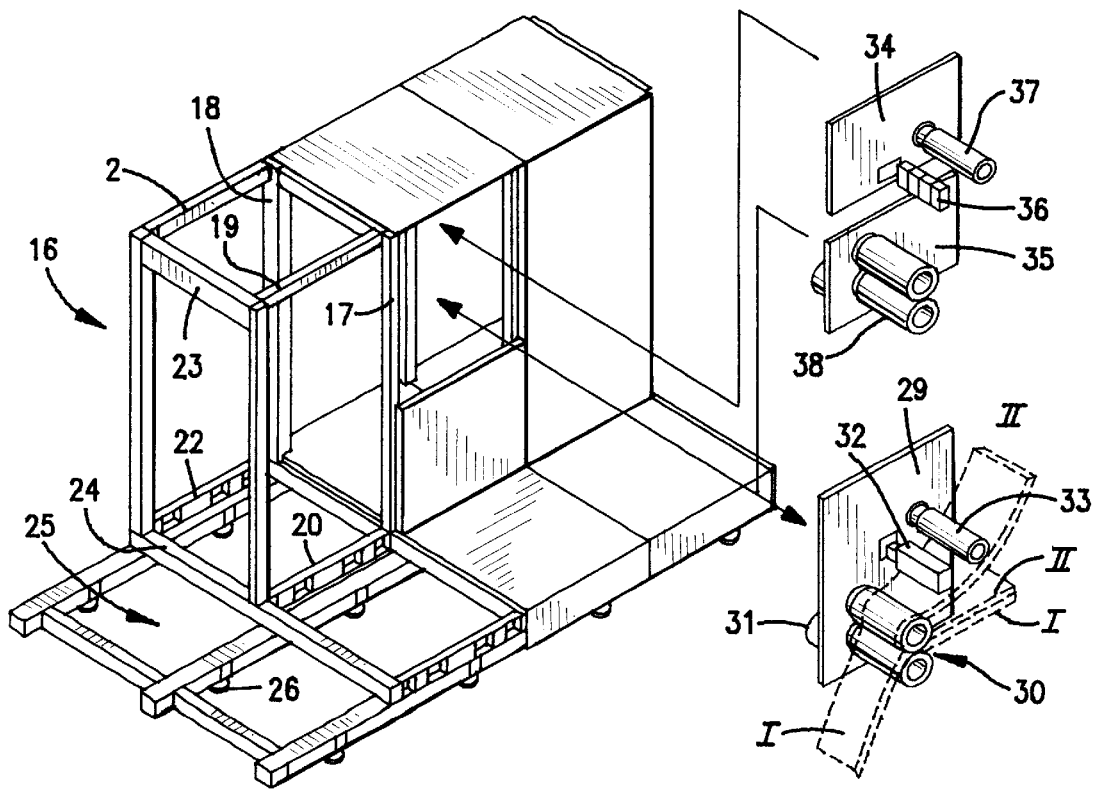
FIG. 2 is a schematic, perspective view taken obliquely from the front of part of the framework and the carrier plates included in the production line illustrated in FIG. 1.
Figure 3:
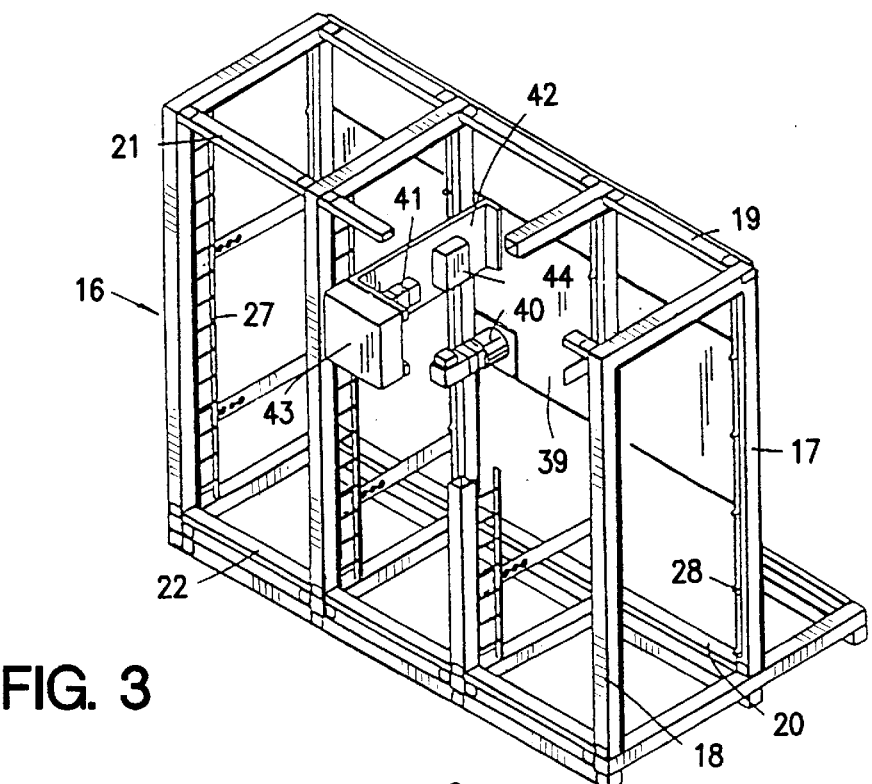
FIG. 3 is a perspective view taken obliquely from the rear of the framework illustrated in FIG. 2.

FIGS. 2 and 3 are respectively schematic, perspective front and rear views of parts of the framework 16 included in the production line. The side of the framework facing the conveyors and the viewer of FIGS. 1 and 2 is the front side of the framework. The framework 16 is constructed from two parallel rows of front and rear vertical posts 17 and 18 respectively, which are evenly spaced in the rows. The mutually sequential posts 17 and 18 in said rows are connected together by top and bottom cross bars 19, 20 and 21, 22 respectively, and mutually opposing posts in the working direction of the production line are joined together by additional top and bottom cross bars 23, 24. Naturally, further cross bars may be included if necessary for mechanical strength reasons, although this is avoided if possible, at least in the front row of posts 17, in order to avoid such cross bars restricting possible positioning of working devices on carrier plates attached to the framework. The bottom cross bars 24 extend beyond the front posts 17. The framework rests on a carrier frame 25 which includes height-adjustable legs 26.

As illustrated schematically in FIG. 3, cable ladders 27 are arranged on the rear vertical posts 13. These cable ladders include heavy-current conductors and weak-current conductors through which current is supplied to the working devices of the production line, and a network cable is also connected to a central computer. Arranged within the front vertical posts 17 are compressed-air lines, and a row of compressed-air outlets 28 is placed along the length of said posts.

As before mentioned, the working devices are carried by carrier plates, which are screwed firmly to the front vertical post 17 of the framework 16. The size of these carrier plates is adapted a large extent to the size of the working device which the plate concerned is intended to carry or support, as indicated in FIGS. 1 and 2, which makes the production line highly flexible. FIG. 2 illustrates an example of how this flexibility can be utilized. The Figure shows a carrier plate 29 which carries a roll pair 30 driven by an alternating current motor 31. The plate 29 also carries a gluing unit 32 provided with a slot-shaped nozzle (not shown) and a guide roller 33. Also shown in FIG. 2, in broken lines, is a first web of material I which is glued to a second web of material II in the nip of the roll pair 30, this web II having passed beneath the glue nozzle of the glue applicator 32 prior to entering the roll nip. If it is later decided that the webs I and II can equally as well be joined together with glue beads, the carrier plate 29 can be removed from the framework 16 quickly and simply and replaced with another carrier plate which supports a different type of glue applicator. In the FIG. 2 illustration, the carrier plate 29 has been replaced with two carrier plates 34 and 35, which carry a glue applicator 36 which includes a row of glue nozzles, and a guide roller 37 and a driven roll pair 38 respectively. The carrier plates 34, 35 have the same width as the carrier plate 29, but are only half as high.

Figure 4:
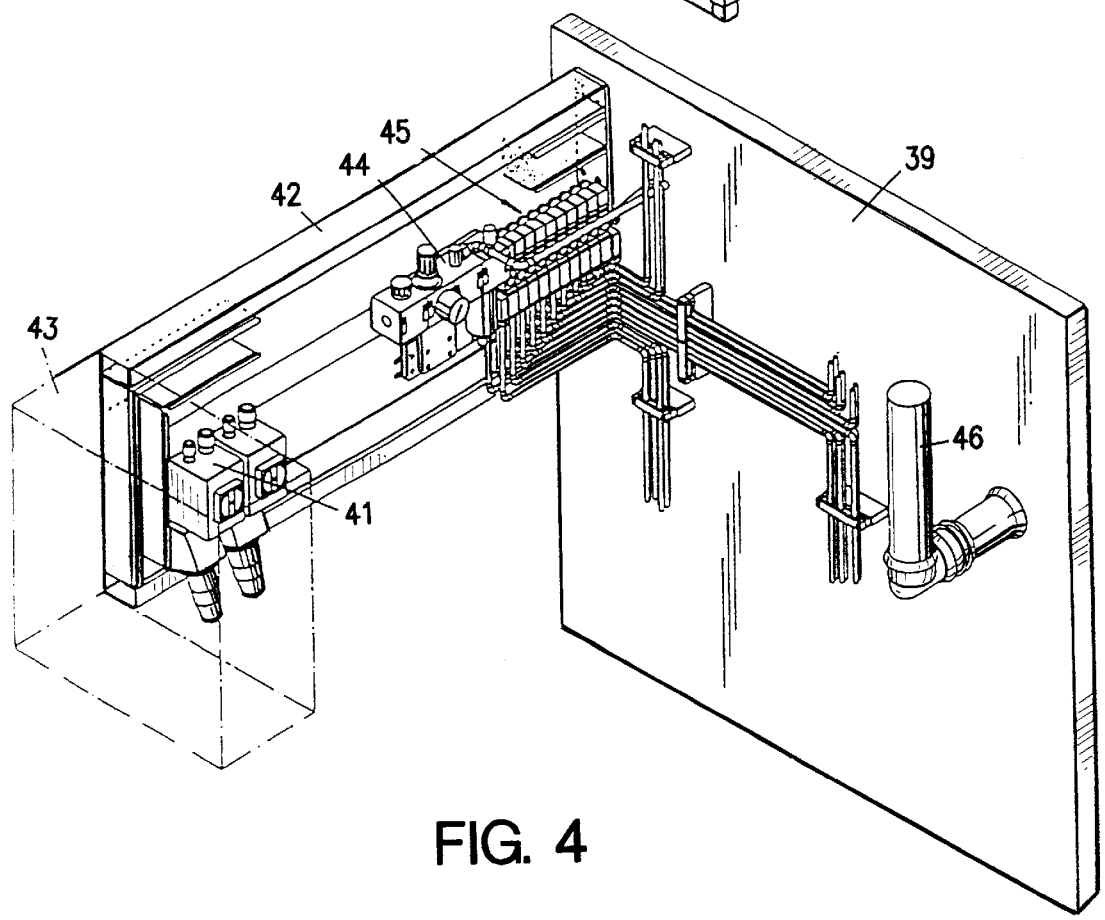
FIG. 4 is a perspective rear view of a carrier plate provided with a connector element holder.

FIGS. 3 and 4 are schematic, perspective rear views of a carrier plate 39 which carries a working device, for instance a driven roll pair, whose drive motor 40 is mounted on the rear side of the carrier plate 39. The drive motor 40 is comprised of an alternating current motor whose output shaft passes through the carrier plate and coacts with the working device (not shown) mounted on the front of the plate. The drive motor is connected, by conductors not shown, to safety switches 41 mounted on a holder 42. The safety switches can, in turn, be connected to the nearest cable ladder 27 on the framework 16, with the aid of appropriate connectors, for instance plug-in connectors. The holders 42 are always arranged in the same position on a carrier plate that carries a working device, more specifically in the upper right-hand corner of the illustrated inventive carrier plate, as seen from the front. As a result, there is only a small distance between holder and the nearest cable ladder, meaning that a short conductor can be used from the holder 42, one end of this conductor being connected to the male part of the plug-in contact. In order to make this length of the conductor short, several female connector parts are spaced in the height direction along the cable ladders.

The holder 42 also carries a control unit 43 by means of which the working device is controlled, this unit, in turn, being connected to a central computer which controls all working devices included in the production line, via the network cable or conductor in the cable ladders. The holder 42 also carries a compressed-air unit 44, which is connected to the nearest compressed-air outlet 28, by means of a suitable hose coupling. As shown schematically in FIG. 4, the unit 44 includes a row of compressed-air valves 45, from which airlines lead to pneumatic piston-cylinder devices (not shown) included in the working devices mounted on the front side of the carrier plate. Pneumatics are normally used to move the working devices into and out of their respective working positions, for instance to move the rolls of a roll pair towards and away from one another, although other applications, such as pneumatic motors, can be used within the scope of the invention. FIG. 4 also shows a pipe 46 which can be connected by means of a suitable hose coupling to a sub-pressure source, for instance a vacuum box, which is often positioned beneath a conveyor in the production line provided with a row of coupling outlets. Naturally, it is also possible to provide a pipe system which is connected to a sub-pressure source in or outside the vertical posts 17 or 18 in a manner similar to the compressed air supply arrangement, or to provide a row of coupling outlets along the posts. As will be understood, hydraulic fluid connections may also be arranged in the rows of connector arrays when hydraulic motors are used in the production line.

As the size of the carrier plates is determined essentially by the size of the working device or devices that the plates are intended to carry, the space for accommodating each working device in the production line is also determined in practice by the size of the device. However, the dimensions of the carrier plates must be proportionate to one another in a particular manner, so as to enable the plates to be exchanged and to achieve the desired flexibility of the production line. Thus, the sizes of the carrier plates must be such as to enable each carrier plate to be replaced with or exchanged for one or more other carrier plates. To this end, the lengths of the sides of the carrier plates are essentially a multiple of the length of the smallest side of the smallest carrier plate, and the carrier plates are so dimensioned that each carrier plate will include a pair of opposing sides whose lengths are generally equal to or generally comprised a multiple of the distance between the posts 17. The fact that the lengths are not exact multiples of the length of the smallest side of the smallest carrier plate is because the carrier plates shall be spaced at a small distance from one another on the framework, so as to make fitting and dismantling of the plates easier, as will be explained in more detail below. For practical reasons, this distance should be at least 2 mm and the length of the smallest side of the smallest plate should be at least 400 mm.

The working devices of the inventive illustrated production line are mounted by placing the carrier plates supporting the working devices included in the production line in place in the framework and screwing the plates securely thereto. The quick-couplings for the delivery of flowing media, i.e. electric current, compressed air, etc., are then coupled to the delivery lines provided in the framework, and the control devices 43 controlling the working devices are connected to the central computer by means of databus connections. The production line is ready to be put into operation when all working devices have been secured and connected-up. Fine adjustment, or trimming, of the fitted working devices is unnecessary, since these devices are constructed as independent units which possess their own drive means and control units, the different operations of which are controlled and synchronized by a central computer. It thus suffices to check that the individual working devices function in the manner intended. It can be mentioned in this regard that when replacing a working device in the production line, for instance replacing a device that has broken down or replacing a device with a more modern device, the function of the device can be readily tested beforehand, outside the production line, therewith making the stand-still time required to change the device as short as possible. Furthermore, adaptation of the size of the carrier plates to the size of associated working devices enables available space on the framework to be utilized more effectively, so that additional working devices can be added to the production line without requiring comprehensive restructuring. Because each working device supporting carrier plate forms an independent unit which can be operated independently, comprehensive restructuring of the production line can also be effected in a very short period of time; in theory, the minimum restructuring time is the time taken to remove a carrier plate and fit another.

The vertical posts 17 included in the framework 16 are preferably secured to the remainder of the framework in a manner which enables the posts to be easily dismantled. This enables posts that are located behind carrier plates of such size as to extend between three sequential posts 17 in the Figures to be dismantled so as not to be in the way of working devices mounted on such a plate. When the plate does not extend along the full height of the framework, a cross bar is suitably fitted between the posts supporting said plate so as to give further support thereto. To this end, the vertical posts are conveniently provided with a row of cross-bar attachments extending along the length of said posts.

The carrier plates, which have a size such that all sides have a length which is equal to or exceeds the distance between the posts 17, are preferably constructed to enable the plates to be fastened to the posts in either one of two positions which are at right angles to one another. This can be achieved, for instance, by providing the plates with rows of penetrating screw-holes or bolt-holes along each edge-part of the plate, these rows of holes coacting with rows of screw-threaded holes on the posts 17.

As indicated in FIGS. 1 and 2, the outer surfaces of the framework 16 are completely clad with carrier plates, even at those places where no working devices are carried. Although not shown in the drawings, strips are arranged in the spaces between mutually adjacent carrier plates. These strips may have the form of sealing strips provided with resilient sealing lips and can be easily fitted and removed. The interior of the framework is thus a closed spaced. This prevents dust and dirt from reaching the operating and control components that are enclosed in this space and, at the same time, enables an appropriate type of cooling unit (not shown in the drawings) to be placed in the centre of the space for central cooling of said components. It is pointed out that the rear and side walls of the framework need not be comprised of carrier plates according to the aforegoing, but may be comprised of conventional wall elements to no disadvantage, wherein a door which provides access to the interior of the framework may be provided in one of these walls. According to one variant, the interior space is placed under a low sub-pressure, to prevent the ingress of dust and dirt.

As shown in FIGS. 2 and 3, the bottom cross-bars 24, which extend forwardly beyond the front posts 17 transversely thereto are also covered with carrier plates. According to one variant of the invention, the conveyors are fastened in these plates by means of quick-couplings, to facilitate fitting of the carrier plates secured to the posts 17.

It will be understood that the described and illustrated exemplifying embodiment of an inventive production line can be modified in many ways within the scope of the invention. For instance, the framework may include props or braces between the posts 18, for supporting heavy bar-projecting working devices, so that the devices will not bend. Correspondingly, props or braces can be attached to the carrier frame 25 on the front side, so as to prevent bending of long rolls. It is also possible to provide the framework with glue delivery connections. Furthermore, the sets of connections may be fitted to solely each alternate rear post 18. In this case, it may be convenient to place the connector holders of two carrier plates which lie adjacent one another in the lateral direction on laterally opposite sides of the carrier plates. Thus, the invention includes all constructions in which the distance between connector sets in said rows of connectors form a multiple of the smallest distance between the vertical posts and those constructions in which the holders are placed on several standardized locations along the edge parts of the plates. The roof of the framework may also be used to support particularly bulky working devices, such as reel racks, for instance. The invention is therefore limited solely by the content of the following claims.

I claim:

1. In a production line for manufacturing absorbent disposable articles selected from the group consisting of diapers, sanitary napkins and incontinence guards, the production line including a conveyor path which functions to move a web of material through the production line, and a row of working devices which are arranged sequentially in the direction of movement of the conveyor path and which function to perform different working operations in the manufacture of the absorbent articles, wherein the working devices are carried by rectangular carrier plates which are fastened to spaced vertical posts, which in a framework are placed on a same side of the conveyor path and sequentially in a direction parallel with the direction of conveyor path movement, the improvement wherein the carrier plates are of mutually different sizes and have sides of different dimensional lengths; the length of each side of a carrier plate is essentially a multiple of the length of the smallest side of the smallest carrier plate; the spacing between the vertical posts is essentially a multiple of the length of the smallest side of the smallest carrier plate; and each carrier plate includes a pair of opposing sides whose lengths are essentially equal to or essentially constitute a multiple of the smallest spacing between the posts.

2. A production line according to claim 1, wherein each working device includes operating means which are carried by a same carrier plate as the working device concerned.

3. A production line according to claim 2, wherein the framework includes at least one row of sets of connectors for delivering flowing media, the connector sets being arranged sequentially in the direction of conveyor path movement and being separated by a distance which is equal to a multiple of the smallest spacing between the vertical posts; each working device mounted on a carrier plate being provided with one or more connector-elements for connection to one or more of the connectors in said connector sets.

4. A production line according to claim 3, wherein each set of connectors provided on the framework includes a databus connection, and each working device includes a control means connectable to the databus connection.

5. A production line according to claim 1, wherein adjacent sides of mutually adjacent carrier plates are attached to the frame work such as to leave a space of at least 2 mm therebetween.

6. A production line according to claim 5, wherein each carrier plate that carries a working device includes a connector-element holder, said holder being placed in a same position on each carrier plate.

7. A production line according to claim 1, wherein the smallest spacing between the framework posts is essentially equal to twice the length of the smallest side of the smallest carrier plate.

8. A production line according to claim 7, wherein the smallest side of the smallest carrier plate has a length of at least 400 mm.

9. A production line according to claim 1, wherein at least one of the carrier plates that carries a working device includes more than one connector-element holder, said holders being placed sequentially along one side-edge part of the carrier plate.

10. A production line according to claim 1, wherein each carrier plate, the sides of which all have a length which is essentially equal to or essentially exceeds the smallest spacing between the posts, can be attached to the framework in at least one first position and one second position, wherein in said second position the carrier plate is turned through 90° in relation to the first position.

11. A production line according to claim 1, wherein the outer sides of the framework are clad with wall elements, and the carrier plates attached to the vertical posts for a wall such as to define a closed space within the framework; and the production line includes means for cooling said space.

* * * * *